US00PP33472P3

(12) United States Plant Patent
Dal Pane

(10) Patent No.: US PP33,472 P3
(45) Date of Patent: Sep. 14, 2021

(54) KIWI PLANT NAMED 'RED GOAL'

(50) Latin Name: ***Actinidia chinensis* Planchon**
Varietal Denomination: RED GOAL

(71) Applicant: SUMMERFRUIT S.r.l., Castel Bolognese (IT)

(72) Inventor: Giampaolo Dal Pane, Castel Bolognese (IT)

(73) Assignee: SUMMERFRUIT S.r.l., Castel Bolognese (IT)

( * ) Notice: Subject to any disclaimer, the term of this patent is extended or adjusted under 35 U.S.C. 154(b) by 0 days.

(21) Appl. No.: 16/873,231

(22) Filed: Feb. 27, 2020

(65) Prior Publication Data

US 2020/0275596 P1 Aug. 27, 2020

(30) Foreign Application Priority Data

Feb. 27, 2019 (QZ) ..... PBR 2019/0552

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
CPC ..... A01H 5/08
See application file for complete search history.

(56) References Cited

U.S. PATENT DOCUMENTS

2008/0155721 P1 6/2008 Mingzhang et al.
2020/0296871 P1 9/2020 Dal Pane

*Primary Examiner* — Kent L Bell

(74) *Attorney, Agent, or Firm* — Marshall, Gerstein & Borun LLP

(57) ABSTRACT

A new and distinct kiwi (*Actinidia chinensis* Planchon) plant named 'RED GOAL', particularly characterized by distinctive size of fruit, late time of maturity for harvesting, and long cold storage life. Other desirable characteristics include fruits with red pulp and green/brown, almost hairless skin.

13 Drawing Sheets

Latin name of the genus and species: *Actinidia chinensis* Planchon plant.

Variety denomination: 'RED GOAL'.

BACKGROUND OF THE INVENTION

The disclosure provides a new and distinct cultivar of kiwi plant, botanically known as *Actinidia chinensis* Planchon, and hereinafter referred to by the name 'RED GOAL'.

The new cultivar is a product of accidental discovery in Italy under the direction of Giampaolo DAL PANE, an Italian citizen. Several seeds of different and unknown origins were planted. The new variety was discovered in Italy in 2016; it is not the result of any known crossing.

Fruit of the new variety was first evaluated in year 2016 with favorable results. After the first evaluation, semi-hardwood cuttings were made of 'RED GOAL' and were grafted onto 'Hayward' and 'Tomuri' (selection 258), as rootstocks. Evaluation, asexual propagation, and grafting all first took place at the nursery in Santa Cristina e Bissone (Pavia), Italy. Subsequent evaluations of the variety through asexual propagation have shown the characteristics to be true to type.

SUMMARY OF THE INVENTION

The cultivar 'RED GOAL' has not been observed under all possible environmental conditions. The phenotype may vary somewhat with variations in environment, such as temperature, day length, and light intensity, without, however, any variance in genotype.

The following traits of 'RED GOAL' have been repeatedly observed and are determined to be the unique characteristics of 'RED GOAL'. These characteristics, in combination, distinguish 'RED GOAL' as a new and distinct *Actinidia chinensis* Planchon plant with respect to other red pulp *Actinidia:*

1. Distinctive size of fruit;
2. Late time of maturity for harvesting; and
3. Long cold storage life.

COMPARISON TO RED PULP *ACTINIDIA*

Plants of the new cultivar 'RED GOAL' are similar to plants of the seed, *Actinidia chinensis* Planchon 'Hong-Yang' (not patented; however, see U.S. Plant patent application Ser. No. 11/645,130 (Pub. No.: US 2008/155721 P1)) and 'Dong Yang' (not patented) in most horticultural characteristics. However, plants of the new cultivar 'RED GOAL' produce fruit several weeks (roughly three weeks) later than 'Hong-Yang' and 'Dong-Hong'. Average fruit size of 'RED GOAL' is about 100 grams compared to other red pulp *Actinidia chinensis* Planchon (e.g. 'Hong-Yang' and 'Dong-Hong') which average fruit weight ranges from about 75 to 80 g. The cold storage life of 'RED GOAL' is about 5 months, whereas for 'Hong-Yang' and 'Dong-Hong' is about 3 months.

COMMERCIAL COMPARISON

'RED GOAL' has fruits with red pulp and green/brown almost hairless skin. On the other hand, 'Hayward' has green pulp and very hairy brown skin.

BRIEF DESCRIPTION OF THE DRAWING

The accompanying (drawings) illustrate the overall appearance of the new *Actinidia chinensis* Planchon 'RED GOAL' plant showing the colors, as true as is reasonably possible with digital reproduction. Colors in the photographs may differ slightly from the color values cited in the detailed botanical description, which accurately describe the color of 'RED GOAL'. All photographs are taken of plants that are approximately 3 years old. The photographs were taken using conventional techniques and although colors may appear different from actual colors due to light reflectance the colors are as accurate as possible by conventional photographic techniques.

DETAILED BOTANICAL DESCRIPTION

Figure 1:
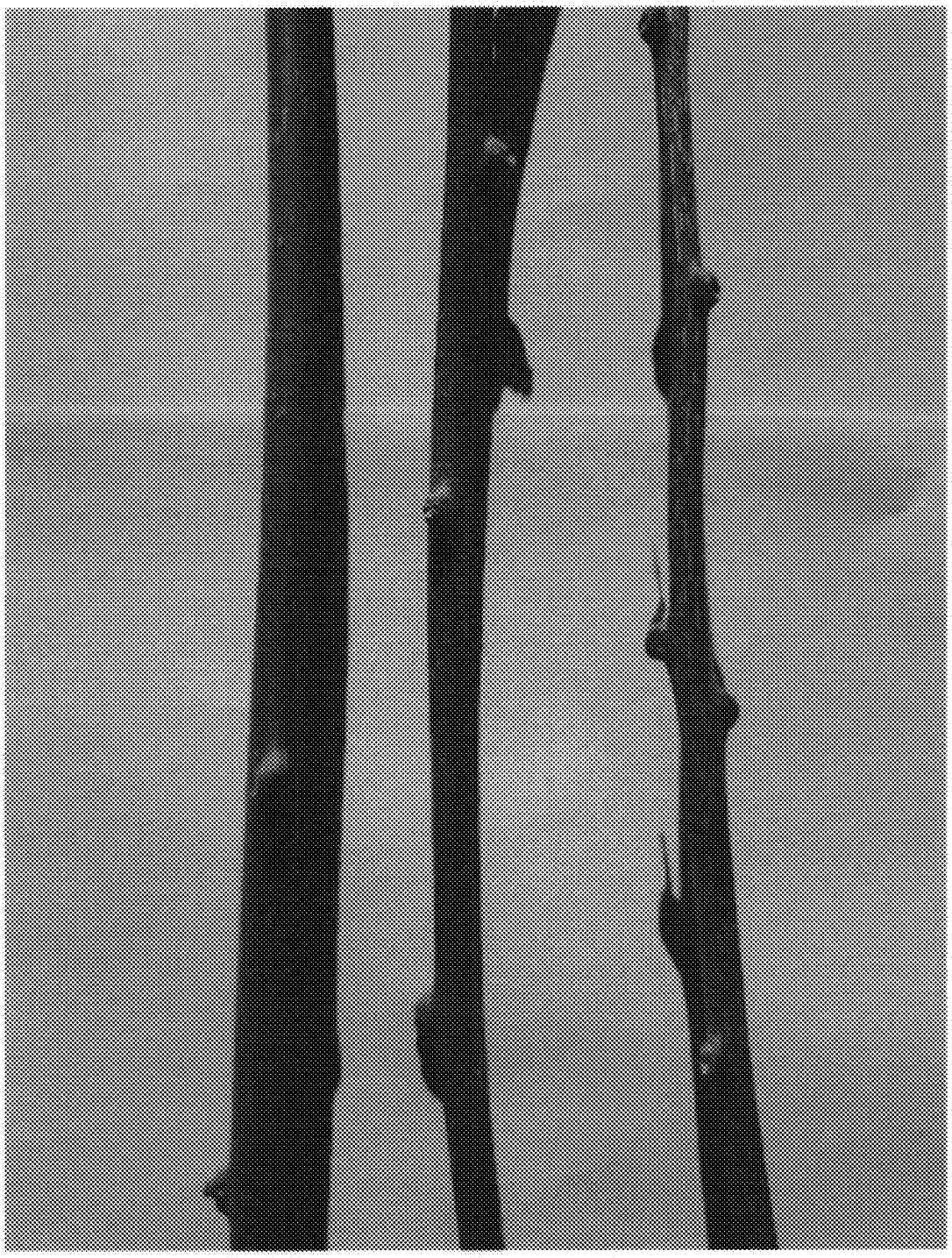
FIGS. 1 and 2 illustrate in full color typical branches and buds on plants of 'RED GOAL'.
Figure 2:
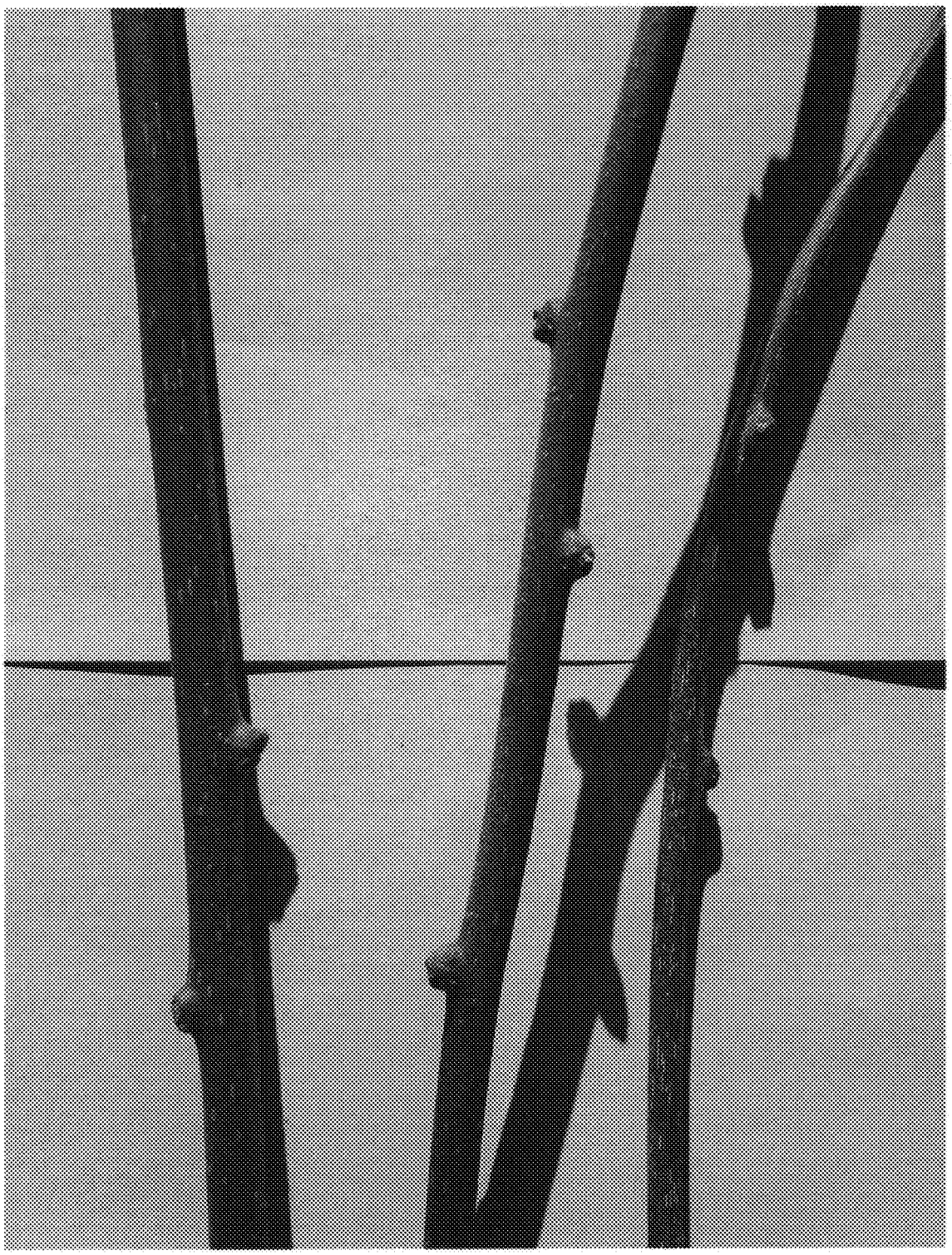
Figure 3:
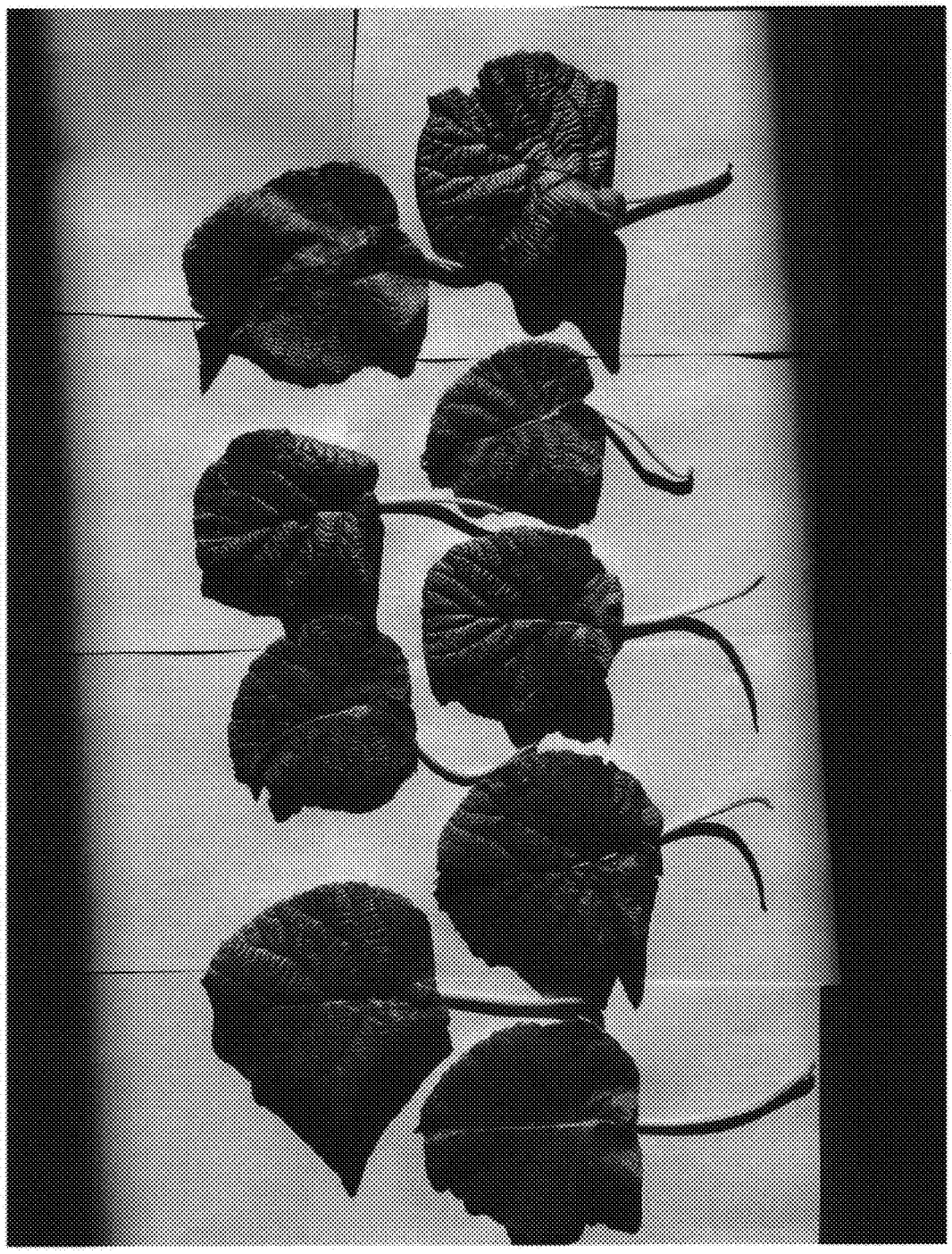
FIGS. 3-4 illustrate in full color typical foliage of 'RED GOAL'.
Figure 4:
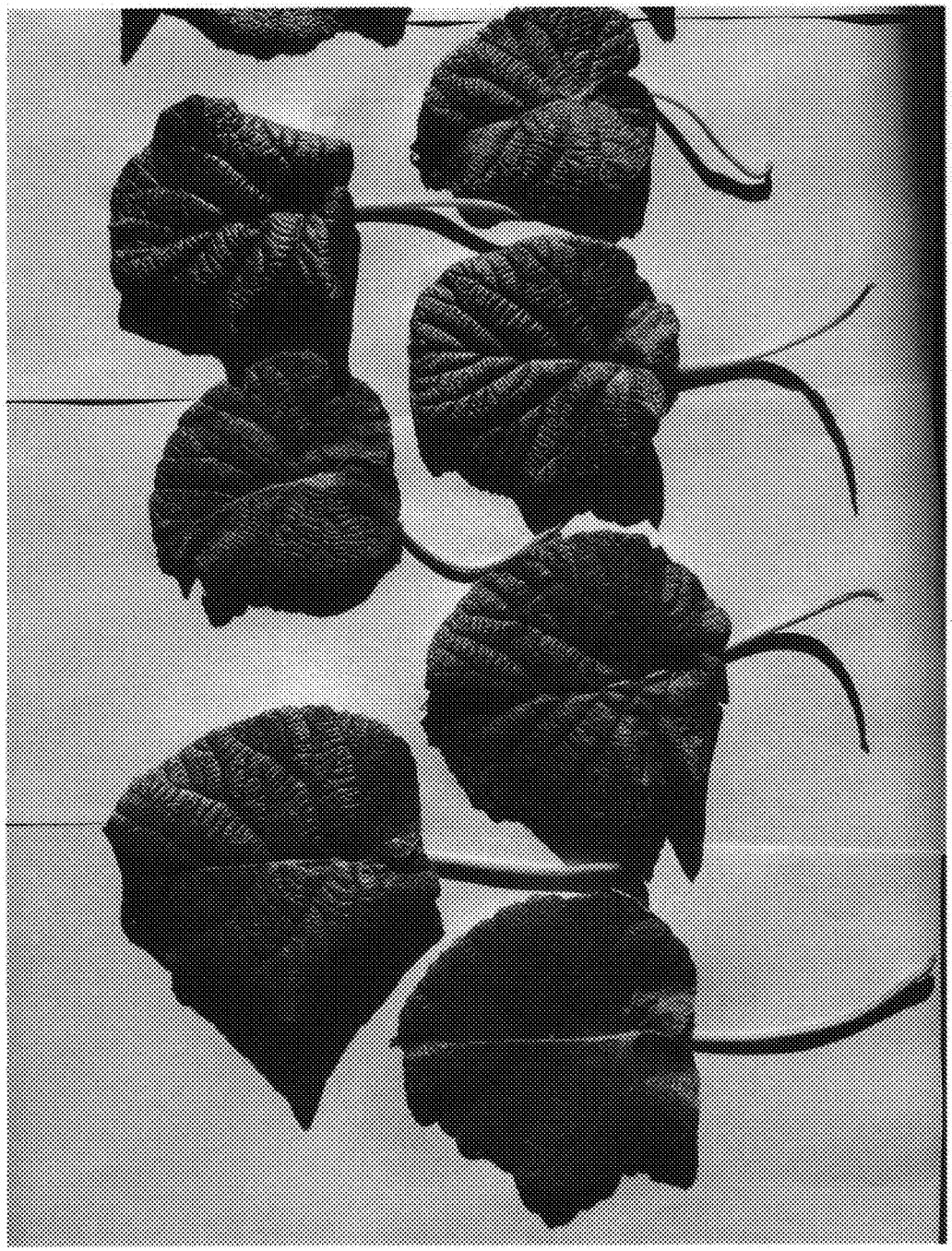
Figure 5:
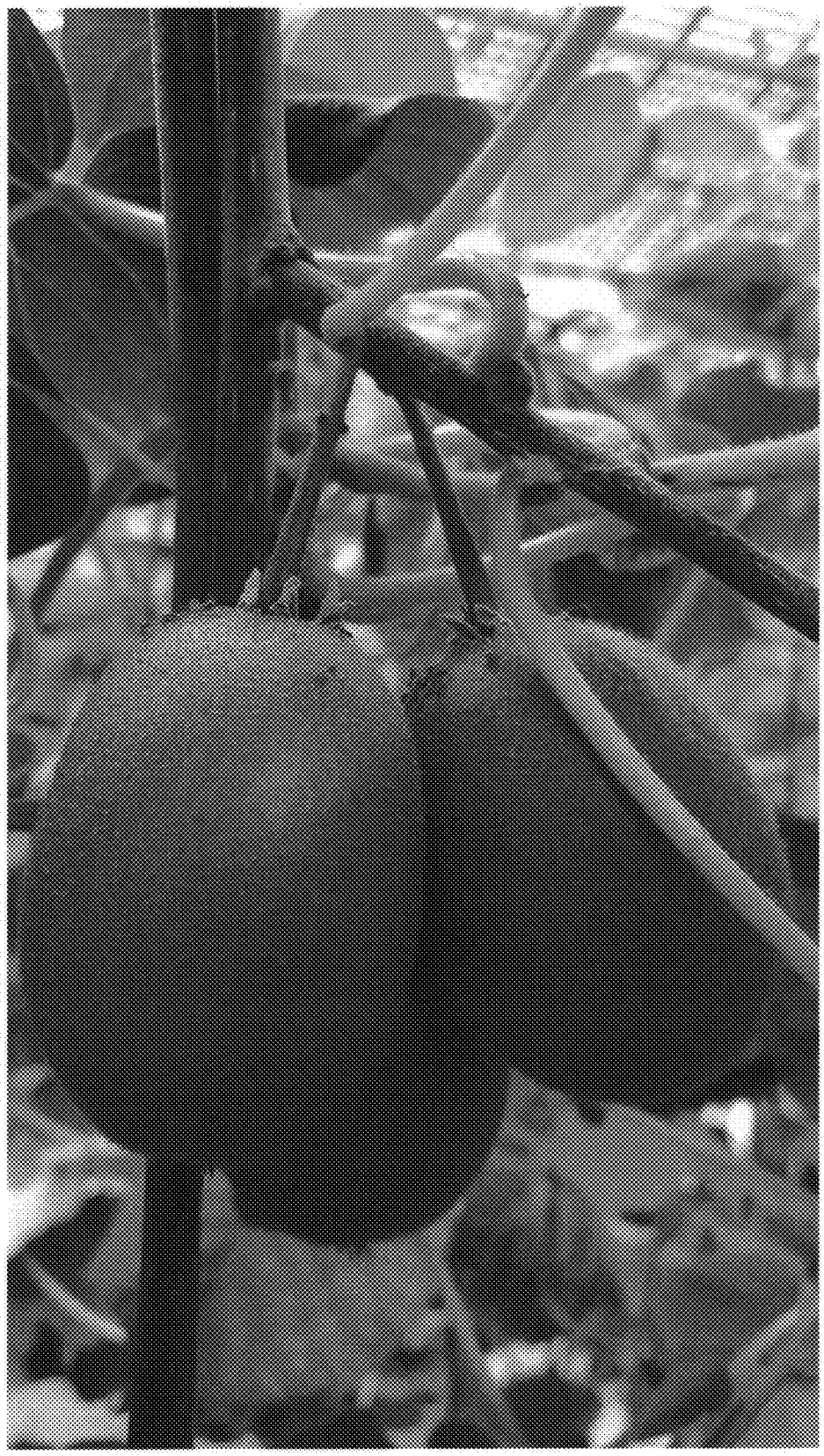
FIGS. 5-8 illustrate in full color typical foliage, hanging fruit, and stems on plants of 'RED GOAL'.
Figure 6:
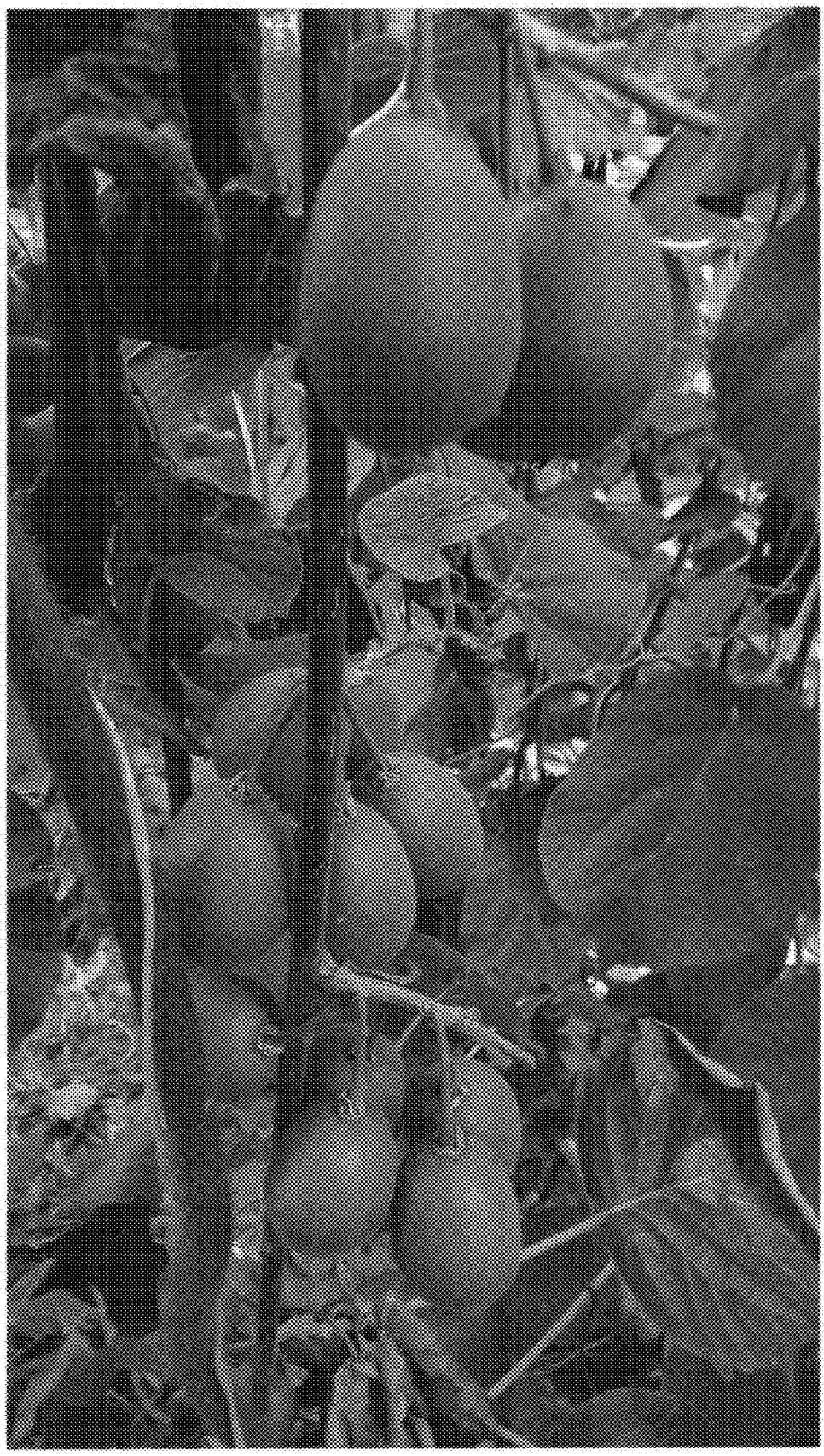
Figure 7:
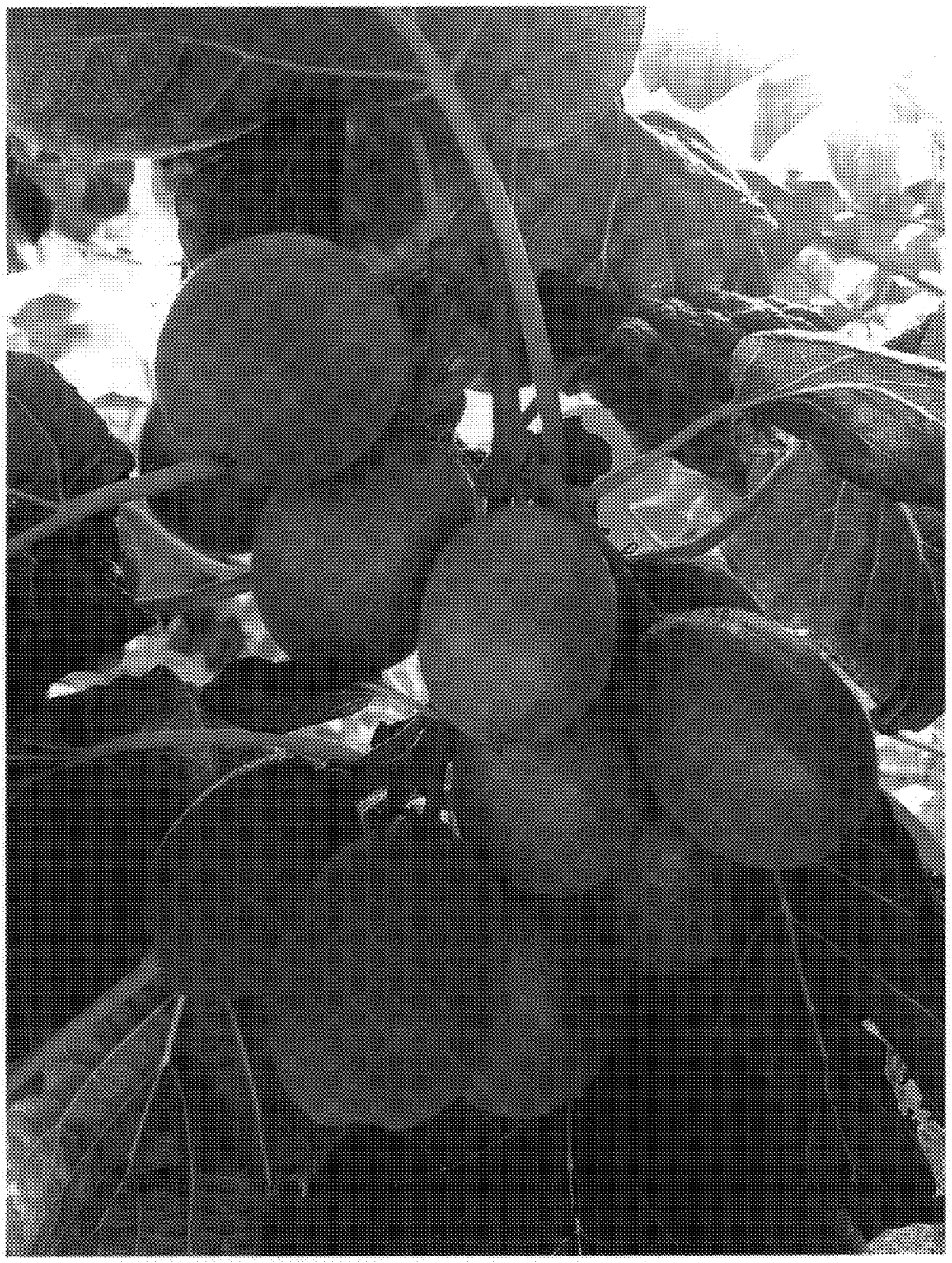
Figure 8:
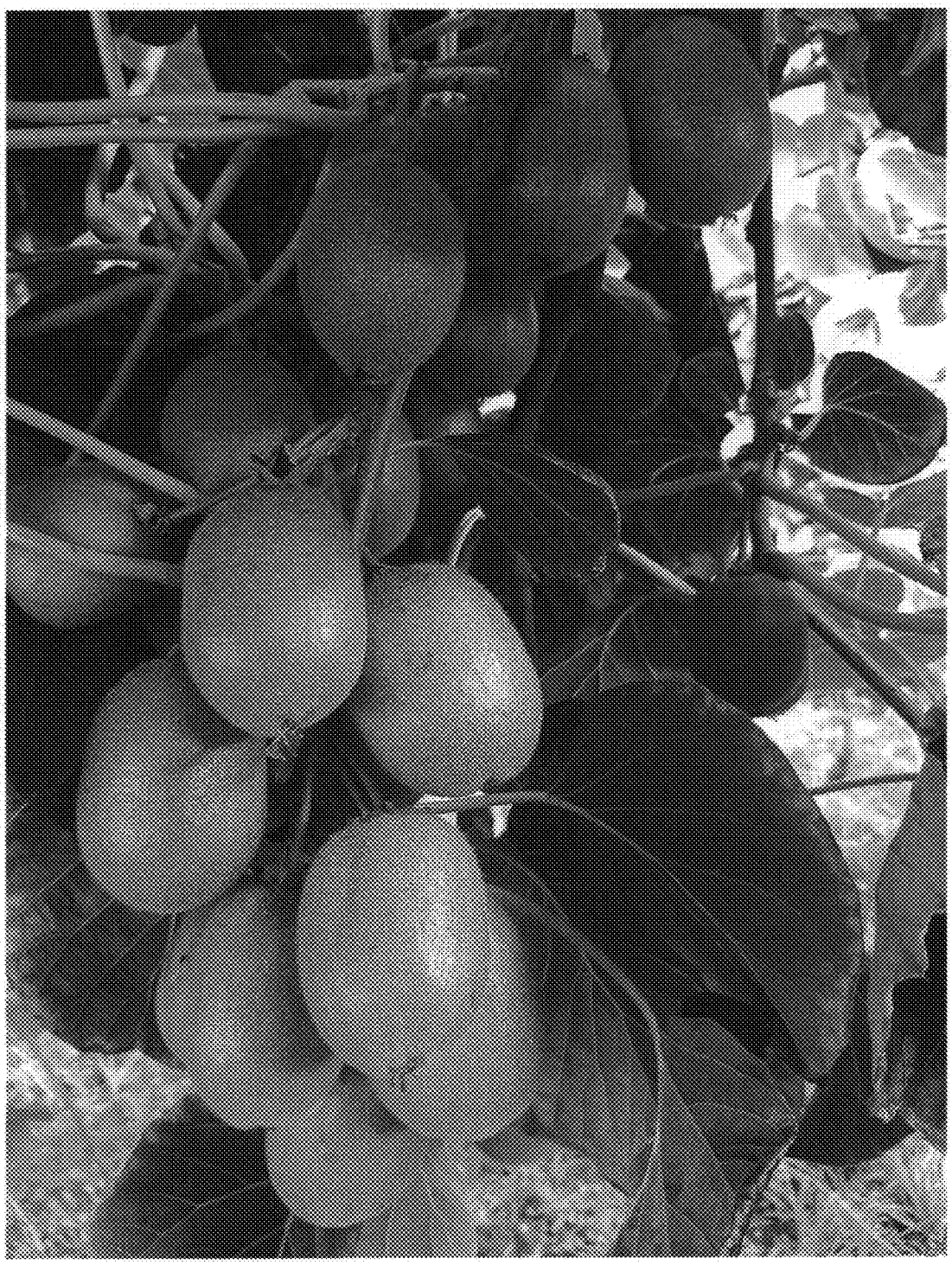
Figure 9:
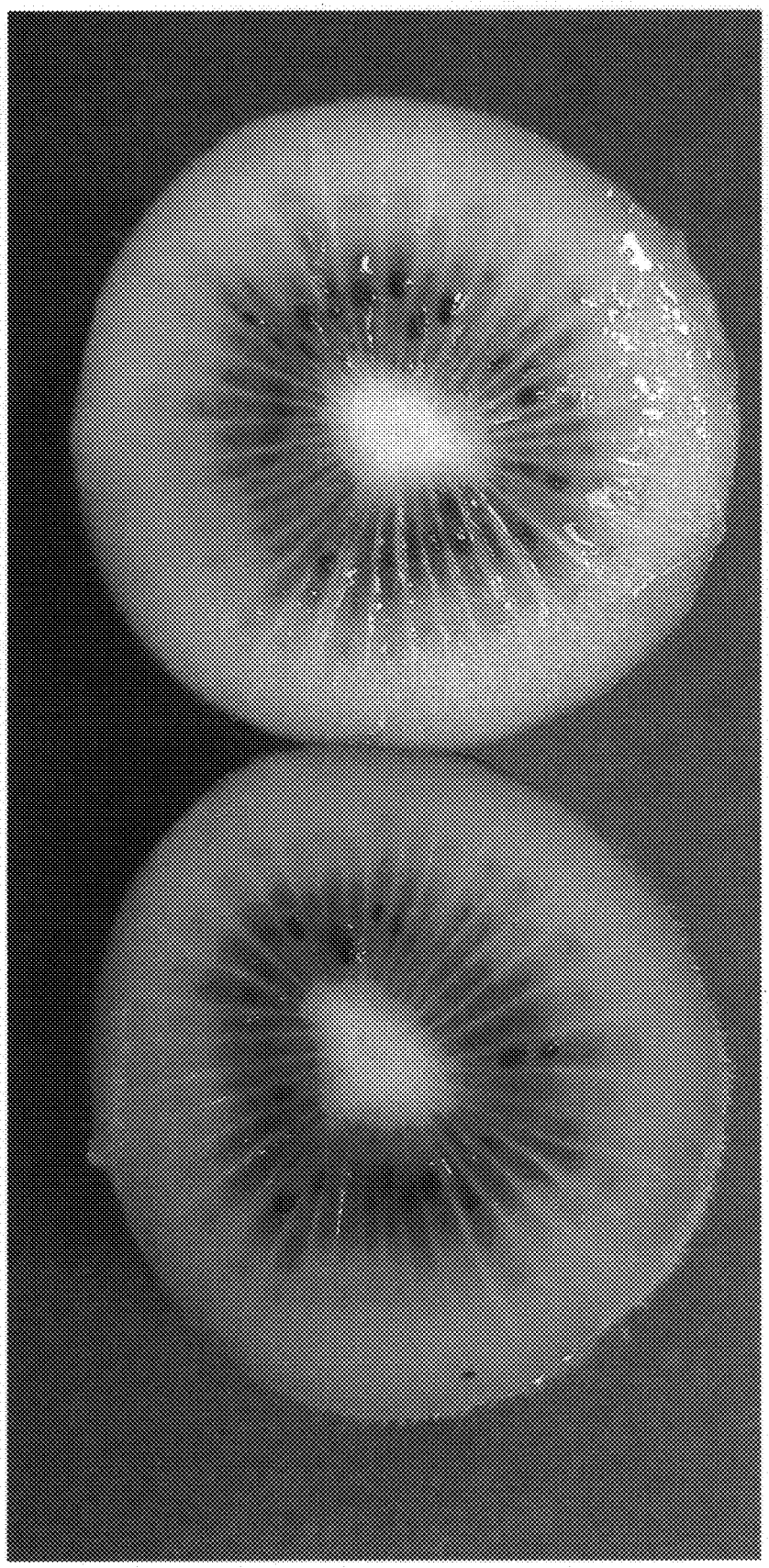
FIGS. 9-11 illustrate in full color typical fruit harvested from 'RED GOAL'.
Figure 10:
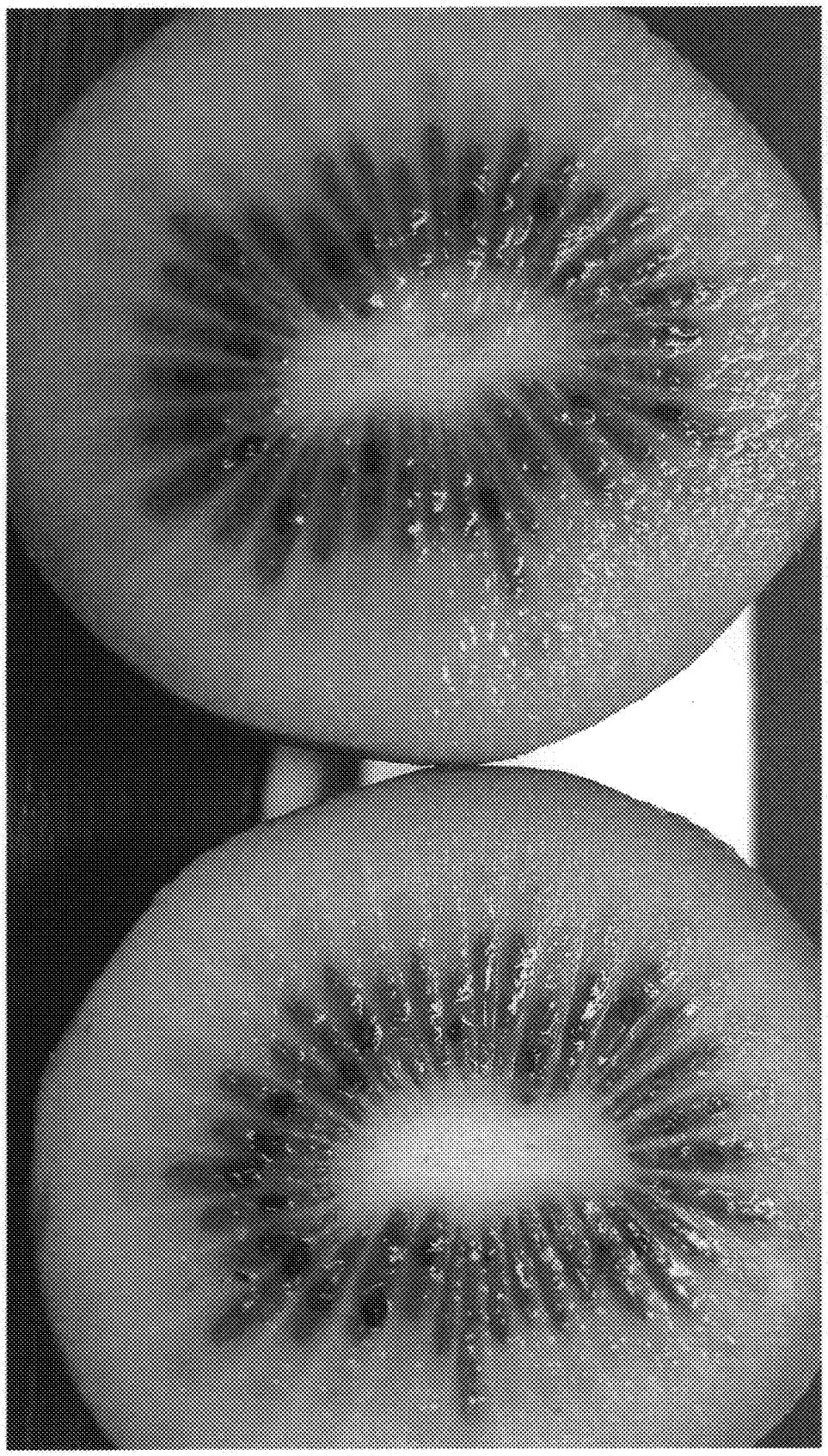
Figure 11:
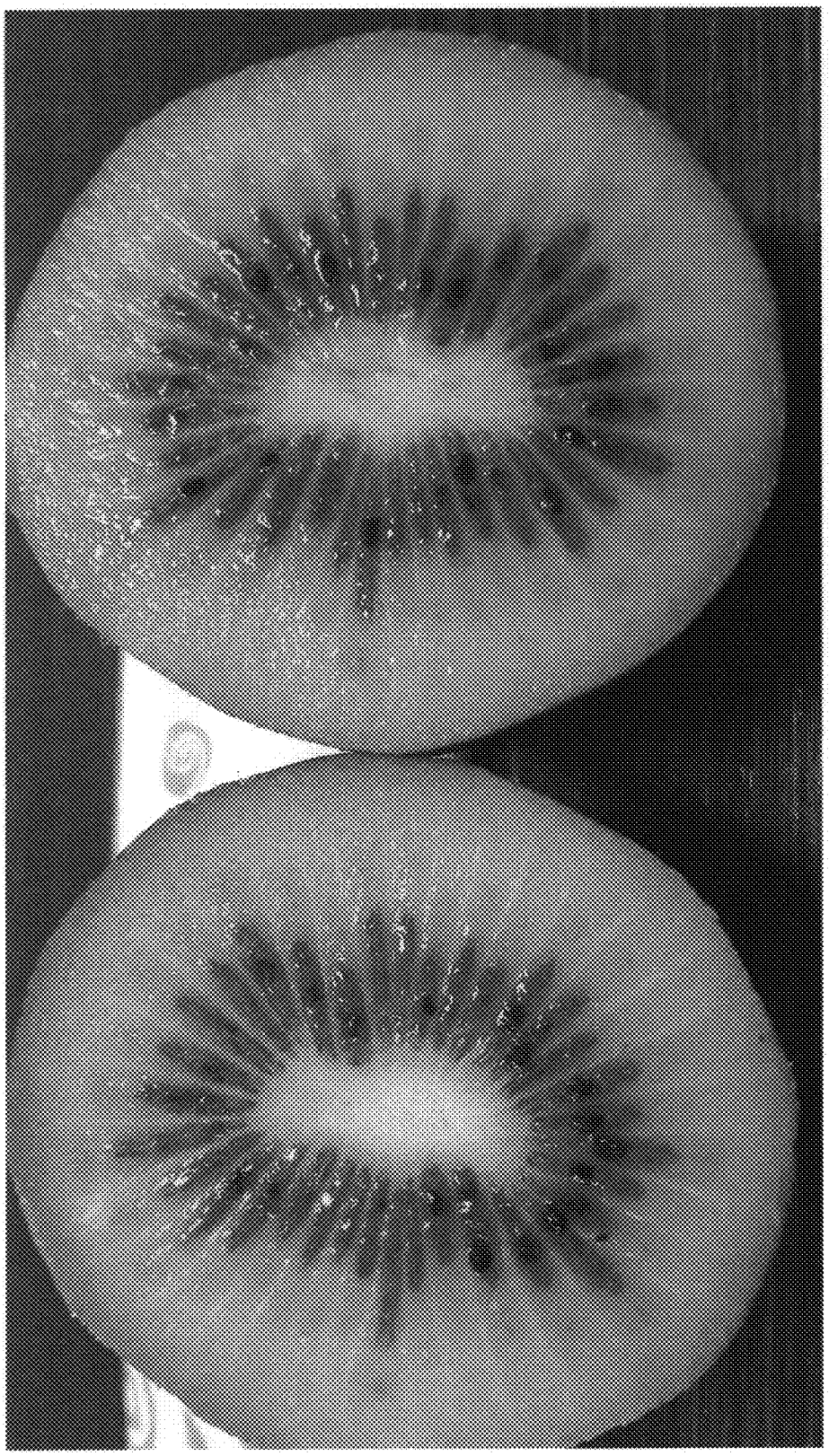
Figure 12:
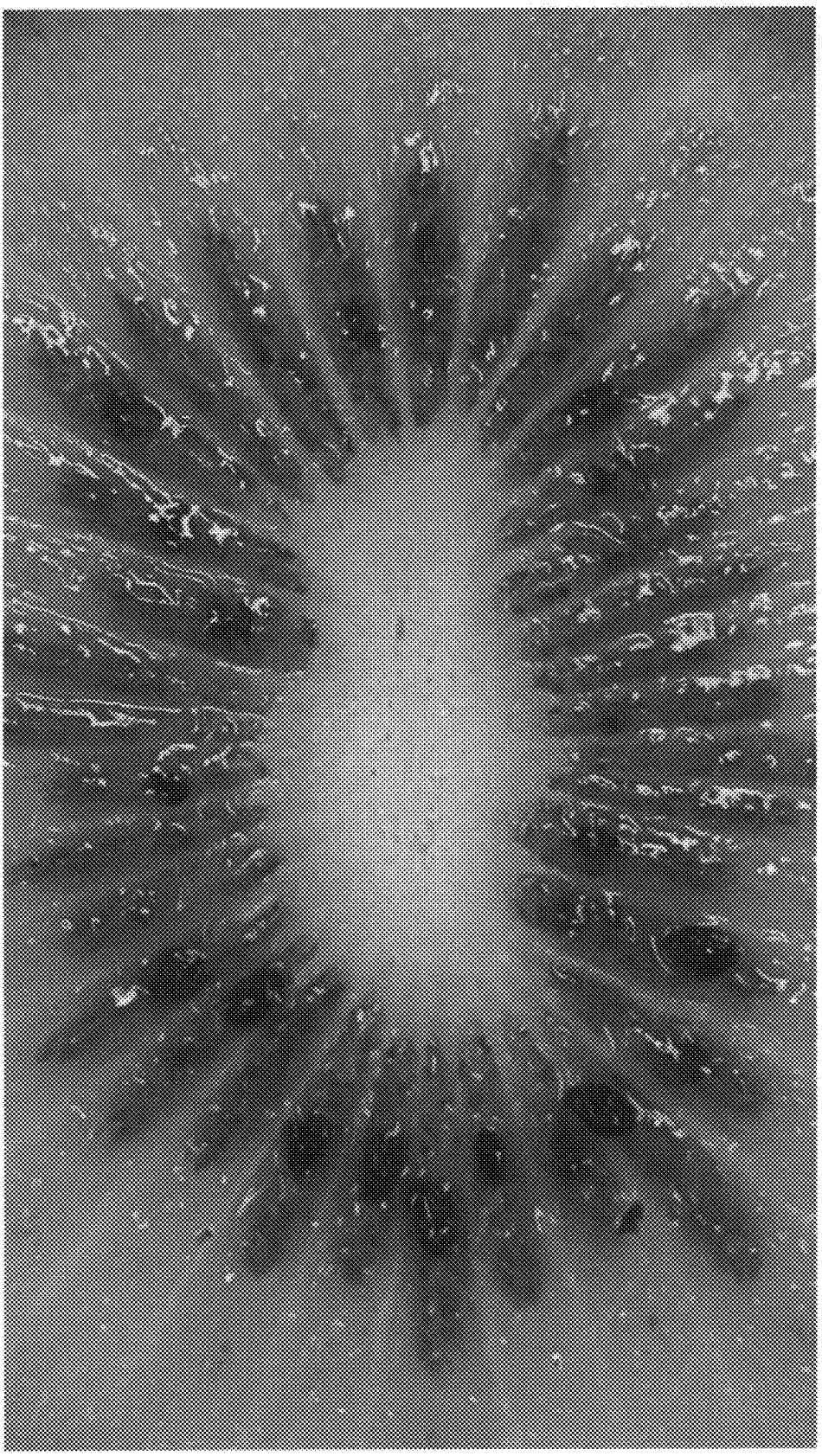
FIG. 12 illustrates in full color an enlargement of the pulp of typical fruit harvested from 'RED GOAL'.
Figure 13:
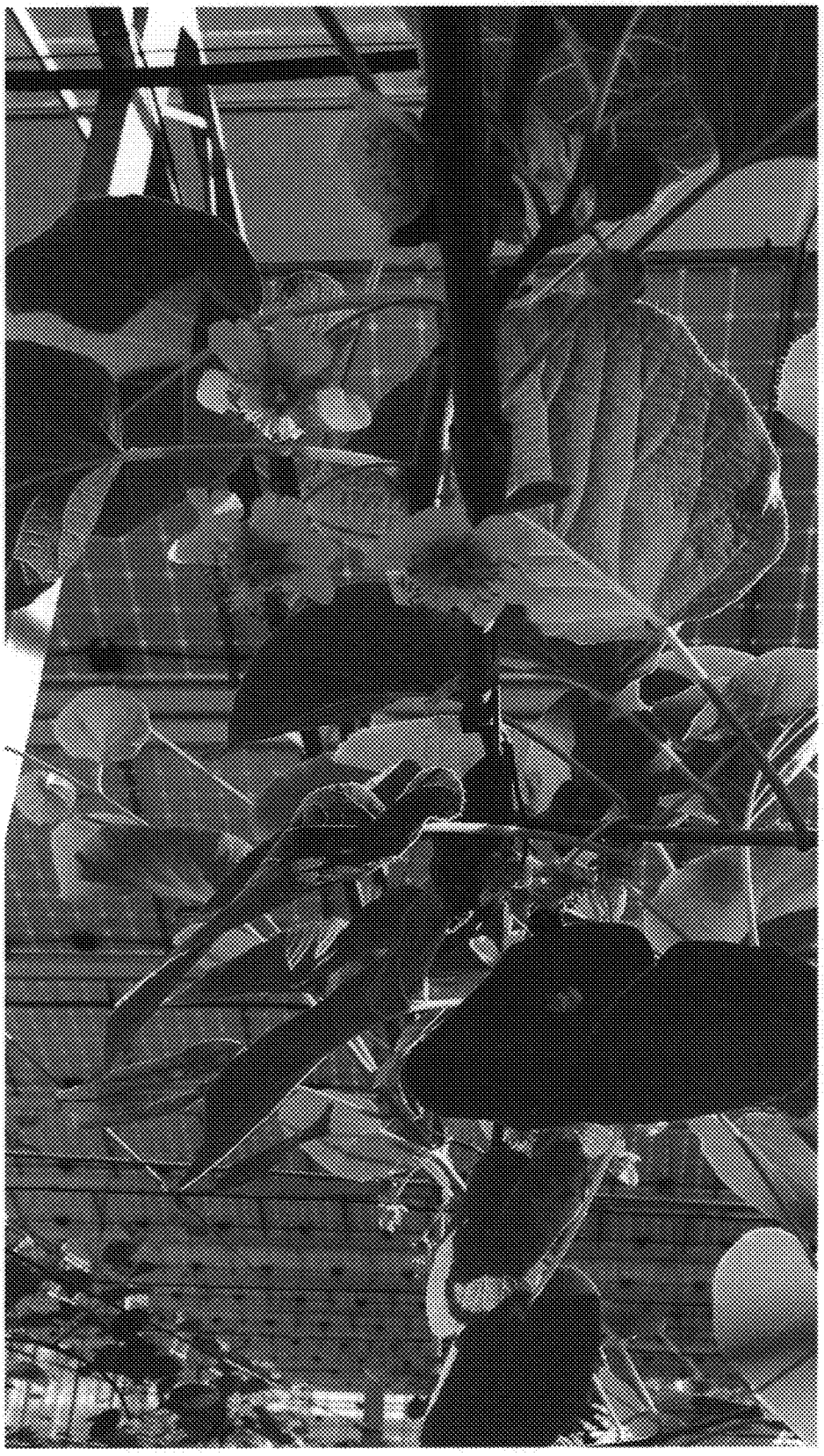
FIG. 13 illustrates in full color flowers of 'RED GOAL'.

The following color references are made to The Royal Horticultural Society Colour Chart except where common dictionary terms are used. The following observations and measurements describe 'RED GOAL' plants grown in greenhouse under commercial trial conditions in Santa Cristina e Bissone (Pavia), Italy. The growing temperature ranged from a minimum of −10° C. in winter (January) up to 40-42° C. in summer (July-August). Annual rainfall is approximately 600 mm per year. Measurements and numerical values represent an average of 10 typical plant types. Botanical classification: *Actinidia chinensis* Planchon 'RED GOAL'.

Classification:

*Botanical.*—*Actinidia chinensis* Planchon.

Propagation: 'RED GOAL' can be successfully grafted onto rootstocks of onto 'Hayward' and 'Tomuri' (Selection 258).

Plant:

*Age of the plant described.*—Approximately 3 years.
*Sex expression.*—Female.
*Ploidy.*—Diploid.
*Plant habit.*—Vigorous, deciduous climber with large leaves and edible fruit.
*Mature plant height.*—Average approximately 8 m.
*Vigor.*—Weak-medium.
*Young shoot color.*—Green. — Near 142A (R.H.S. color chart).
*Young shoot texture.*—Density of hair medium.
*Young shoot length.*—Average approximately 150 cm.
*Young shoot diameter.*—Average approximately 10 mm.
*Mature lateral branches length.*—Average approximately 5 m.
*Mature lateral branches diameter.*—Average approximately 22 mm.
*Mature lateral branches texture.*—Near 144A (R.H.S. color chart).
*Cane length.*—Average approximately 4 m.
*Cane color.*—Near 165A (R.H.S. color chart).
*Cane diameter.*—Average approximately 0.3-0.4 cm.
*Cane texture.*—Substantially no hair.
*Bark texture.*—Substantially no hair.
*Bark color.*—Near 166 A (R.H.S. color chart).
*Trunk diameter.*—Average approximately 3 cm in 3 year-old plant.
*Stem lenticels.*—Average of approximately 35 lenticels (in a space of 5 cm on the stem), irregularly spaced and sized. Oblong in shape, color grey-green. — Near 148D (R.H.S. color chart). Diameter average of approximately 0.25 mm with a depth average of approximately 0.20 mm.

Foliage:

*Leaf.*—Length. — Approximately 2.5-16 cm; Average length. — Approximately 12 cm.
*Width.*—Approximately 10-14 cm; Average width. — Approximately 10 cm.
*Shape of blade.*—Obovate.
*Apex.*—Cuspidate and rounded.
*Base.*—The two mirror part that composes the base presents a round shape in the farthest part of the leaf, which presents a progressive approach to the apex going near to the dibrid.
*Attachment.*—Petioled.
*Margin.*—Line jagged and corrugated.
*Texture of top surface.*—Smooth hairless.
*Texture of underside.*—Pubescent, slightly velvety.
*Color.*—Mature foliage under side: Green. — Near 129D (R.H.S. color chart). Mature foliage upper side: Green near 127B (R.H.S. color chart).
*Leaf venation.*—Pinnate leaf venation pattern. Upper side color. — Near 133A (R.H.S. color chart). Under side color. — Near 130D (R.H.S. color chart).
*Petiole.*—Length: Average length approximately 8 cm; Average diameter approximately 5 mm.

Flower:

*Flowers per inflorescence.*—Normally one.
*Bud color.*—Green. — Near 134B (R.H.S. color chart).
*Bud break.*—Mid-March.
*First flower.*—End-April.
*Flower depth.*—Average approximately 1.5-1.8 cm.
*Natural flowering season.*—End-April to Early-May.
*Diameter.*—Average approximately 4-4.2 cm.
*Petal quantity.*—Average 5-7 per flower. Apex curvature: weakly expressed (rounded apex).
*Petal overlapping.*—Petals touching, sometimes slightly overlapping.
*Petal shape.*—Salverform pattern.
*Petal length.*—Average approximately 16.5 cm.
*Petal width.*—Average approximately 12.4 cm.
*Petal margin.*—Twisted.
*Petal apex.*—Cuspidate and rounded.
*Petal base.*—The base line goes more near to the apex when it approaches the dibrid.
*Petal texture.*—Smooth, hairless.
*Petal color.*—Near 128D (R.H.S. color chart).

*Filament color*.—White. — Near 122D (R.H.S. color chart).
*Anther color*.—Yellow-green. — Near 140D (R.H.S. color chart).
*Anther attitude of styles*.—Semi-erect.
*Anther style color*.—White. — Near 128D (R.H.S. color chart).
*Hair on ovary*.—Pubescent, slightly velvety.
*Color of ovary*.—White-yellow. — Near 145D (R.H.S. color chart).
*Ovary shape*.—Oval shape.
*Pistil number*.—Average approximately between 40-50 per flower.
*Pistil length*.—Average approximately 1.0-1.2 cm.
*Pistil color*.—Near 150D (R.H.S. color chart).
*Stigma length*.—Average approximately 1.5-1.8 cm.
*Stigma width*.—Average approximately 1 mm.
*Number of sepals*.—Average 6.
*Color of sepals*.—Green. — Near 141B (R.H.S. color chart).
*Sepal width*.—Average approximately 6.4 cm.
*Sepal length*.—Average approximately 9.0 cm.
*Sepal texture*.—Smooth.
*Sepal shape*.—Stellate.
*Sepal apex*.—Cuspidate and rounded.
*Sepal margin*.—Twisted.
*Peduncle*.—Length. — Average approximately 4 cm; Color. — Yellow-green. — Near 142B (R.H.S. color chart); Texture. — Smooth (slightly pubescent).
*Peduncle diameter*.—Average approximately 2 mm.

Fruit:

*Color outer pericarp*.—Yellow. — Near 154B (R.H.S. color chart).
*Color inner pericarp*.—Red. — Near 33A (R.H.S. color chart).
*Core color*.—White. — Near 36D (R.H.S. color chart).
*Brix at consumption*.—Average approximately 19.0 degrees Brix.
*Brix at harvest*.—Average approximately 8.5 degrees Brix.
*Brix at the beginning of september*.—Average approximately 6 degrees Brix.
*Average weight*.—Approximately 100 grams.
*Minimum weight*.—Approximately 70 grams.
*Maximum weight*.—Approximately 120 grams.
*Fruit firmness at harvest*.—Average approximately 5 $kg/cm^2$.
*Flesh texture*.—Soft.
*Flesh aroma*.—Excellent. Slight hint of tropical fruits.
*Plant natural harvest season*.—Beginning to middle of October.
*Length*.—Average approximately 6.5 cm.
*Width*.—Average approximately 5.5 cm.
*Locule number*.—Average approximately 40 per fruit.
*Locule length*.—Average approximately 4 mm.
*Locule width*.—Average approximately 0.5 mm.
*Core diameter* (*maximum*).—Approximately 3 cm.
*Core diameter* (*minimum*).—Approximately 1 cm.
*Fruit peduncle length*.—Average approximately 4.2 cm.
*Fruit peduncle width*.—Average approximately 0.3 cm.
*Fruit peduncle color*.—Near 163D (R.H.S. color chart).
*General fruit shape*.—Oblong.
*Shoulder fruit shape*.—Obovate (slightly pear shaped with the top slightly less wide than the bottom).
*Calyx ring*.—Present.
*Calyx ring expression*.—Weakly-expressed.
*Skin color at harvest*.—With more sun, the color is more brown. — Near 156B (R.H.S. color chart). With less sun, the color is more green-yellow. — Near 153D (R.H.S. color chart).
*Hair on fruit skin*.—Pubescent, small and short hair.
*Hair adherence to skin*.—Weak.
*Skin adherence to flesh at maturity*.—Moderate.
*Fruit core shape*.—Transversely oblate.
*Core-woody spike*.—Absent.
*Lenticels on fruit*.—Minute, moderate in quantity, colored yellow-green. — Near 151B (R.H.S. color chart).
*Mature seed color*.—Black. — Near 203D (R.H.S. color chart).
*Dried seed color*.—Brown. — Near 199B (R.H.S. color chart).
*Usual harvest time*.—Approximately October $10^{th}$-20th.
*Overall cropping quantity*.—30 tons per hectare.
*Fruit shelf life*.—Average approximately 5 months after harvest at 1° C. Average approximately 1 month after harvest at 20-25° C.

Other characteristics:

*Storage life*.—Storage life is about 5 months at 1° C.
*Disease/pest resistance*.—Neither resistance, nor susceptibility to pathogens and pests common to *Actinidia chinensis* Planchon have been observed.
*Temperature tolerance*.—Tolerates low temperatures to approximately −5° C. (in winter, not in spring) and higher without negative effects; tolerates high temperatures to approximately 40° C. without negative effects.

What is claimed is:

1. A new and distinct variety of kiwi (*Actinidia chinensis* Planchon) plant named 'RED GOAL', as illustrated and described herein.

* * * * *